US012800458B2

(12) United States Patent
Zheng et al.

(10) Patent No.: US 12,800,458 B2
(45) Date of Patent: Nov. 17, 2026

(54) SHEAR BOX FOR TESTING SHEAR-SEEPAGE COUPLING CHARACTERISTICS OF ROCK MASS, AND METHOD OF USING THE SHEAR BOX

(71) Applicant: INSTITUTE OF GEOLOGY AND GEOPHYSICS, CAS, Beijing (CN)

(72) Inventors: Bowen Zheng, Beijing (CN); Shengwen Qi, Beijing (CN); Jin Zhang, Beijing (CN); Yiqing Zhao, Beijing (CN); Wei Lu, Beijing (CN); Guangming Luo, Beijing (CN); Yongchao Li, Beijing (CN); Wang Zhang, Beijing (CN); Bo Wan, Beijing (CN); Jianing Cong, Beijing (CN); Songfeng Guo, Beijing (CN); Ning Liang, Beijing (CN); Lei Xue, Beijing (CN); Guoliang Li, Beijing (CN); Yu Zou, Beijing (CN); Weiwei Zhu, Beijing (CN); Xiaokun Hou, Beijing (CN); Lina Ma, Beijing (CN); Xin Yu, Beijing (CN); Zifang Zhu, Beijing (CN)

(73) Assignee: INSTITUTE OF GEOLOGY AND GEOPHYSICS, CAS, Beijing (CN)

( * ) Notice: Subject to any disclaimer, the term of this patent is extended or adjusted under 35 U.S.C. 154(b) by 224 days.

(21) Appl. No.: 18/911,508

(22) Filed: Oct. 10, 2024

(65) Prior Publication Data

US 2026/0009708 A1 Jan. 8, 2026

(30) Foreign Application Priority Data

Jul. 2, 2024 (CN) ........................ 202410873527.9

(51) Int. Cl.
*G01N 3/24* (2006.01)
*G01N 33/24* (2006.01)

(52) U.S. Cl.
CPC ............... *G01N 3/24* (2013.01); *G01N 33/24* (2013.01)

(58) Field of Classification Search
None
See application file for complete search history.

(56) References Cited

FOREIGN PATENT DOCUMENTS

| | | | | |
|---|---|---|---|---|
| CN | 114509353 A | * | 5/2022 | ............... G01N 3/02 |
| CN | 219284844 U | * | 6/2023 | |

OTHER PUBLICATIONS

Notification to Grant Patent Rights from CN 202410873527.9 dated Aug. 1, 2024 (2 pages).

* cited by examiner

*Primary Examiner* — Eric S. McCall
*Assistant Examiner* — Nigel H Plumb
(74) *Attorney, Agent, or Firm* — Tutunjian & Bitetto, P.C.

(57) ABSTRACT

A shear box for testing shear-seepage coupling characteristics of rock mass, and a method of using the shear box are provided, including an upper fixed shear box, and a lower movable shear box. A first extrusion block and an upper rock mass sample are arranged in a first placement groove of the upper fixed shear box. A second extrusion block and a lower rock mass sample are arranged in a second placement groove of the lower fixed shear box. A first elastic sealing member is arranged on each of both sides of the upper rock mass sample and the lower rock mass sample, and an elastic capsule is arranged on each of inner walls of both sides of the first placement groove and the second placement groove. An upper pressure head device for applying a force in a third direction is arranged on the upper fixed shear box.

9 Claims, 4 Drawing Sheets

SHEAR BOX FOR TESTING SHEAR-SEEPAGE COUPLING CHARACTERISTICS OF ROCK MASS, AND METHOD OF USING THE SHEAR BOX

CROSS-REFERENCE TO RELATED APPLICATION

This patent application claims the benefit and priority of Chinese Patent Application No. 2024108735279 filed with the China National Intellectual Property Administration on Jul. 2, 2024, the disclosure of which is incorporated by reference herein in its entirety as part of the present application.

TECHNICAL FIELD

The present disclosure relates to the technical field of rock mass engineering geomechanics tests, and in particular to a shear box for testing shear-seepage coupling characteristics of rock mass, and a method of using the shear box.

BACKGROUND

In the geological utilization and storage projects of carbon dioxide, carbon dioxide is injected into the ground in a supercritical state, and makes a multiphase-field long-term coupling reaction with reservoir rock mass, involving complex rock mass engineering geomechanics process. In this process, the research on the mechanical behavior of shear cracks in rock mass induced by supercritical carbon dioxide ($ScCO_2$) in the process of pressing crack or migration is the focus of carbon dioxide enhanced conventional/unconventional oil and gas, saline water, geothermal resource exploitation and long-term safe storage project. It is the most direct and effective way to quantitatively characterize the shear seepage of rock mass in the geological utilization and storage projects of carbon dioxide by studying the shear-$ScCO_2$ seepage coupling characteristics of rock mass through laboratory tests.

Shear box is a key component of a testing device for a direct shear test of rock mass, and plays the role of accommodating samples and transmitting loads. In the process of testing the shear-$ScCO_2$ seepage coupling characteristics of rock mass, since the test scene is a long-term coupling environment of solid-liquid-gas-supercritical and temperature-seepage-stress-chemistry multiphase fields, especially under the simulated working conditions such as $ScCO_2$ enhanced deep oil and gas exploitation, pressure in the test is high, and under the simulated working conditions such as $ScCO_2$ enhanced saline aquifer exploitation, the carbon dioxide is fused with aqueous solution to form an acidic environment, which is highly corrosive to the test device. Therefore, higher requirements are put forward for the sealing performance and corrosion resistance of the shear box. In Patents CN2192848444U and CN114509353A, the related technologies have been tried and explored, but the research requirements of sealing and corrosion resistance in the shear test process of rock mass under $ScCO_2$ seepage cannot be completely satisfied. Therefore, there is an urgent need to develop a shear box for testing shear-seepage coupling characteristics of rock mass.

SUMMARY

An objective of the present disclosure is to provide a shear box for testing shear-seepage coupling characteristics of rock mass and a method of using the shear box, so as to solve the problems in the prior art, and to provide strong sealing and corrosion resistance for a direct shear test system of rock mass under a seepage condition.

To achieve this objective above, the following technical solutions are provided in the present disclosure:

A shear box for testing shear-seepage coupling characteristics of rock mass includes an upper fixed shear box, a lower movable shear box, and a connection limiting part.

A length direction of the upper fixed shear box is taken as a first direction, a width direction of the upper fixed shear box is taken as a second direction, the first direction is perpendicular to the second direction, and a third direction is perpendicular to both the first direction and the second direction.

The connection limiting part includes two inverted U-shaped frames, and the two inverted U-shaped frames are arranged in sequence in the first direction, and both ends of a bottom of each of the two inverted U-shaped frames are fixed to both sides of the lower movable shear box, respectively. The lower movable shear box is located below the upper fixed shear box, one end of the upper fixed shear box is capable of sliding into the inverted U-shaped frame above the lower movable shear box in the first direction.

A first placement groove with a downward opening is arranged in the upper fixed shear box, and a second placement groove with an upward opening is arranged in the lower movable shear box. The opening of the first placement groove is communicated with the opening of the second placement groove. A first extrusion block is arranged in the first placement groove, and the first placement groove at one side of the first extrusion block is configured for placing an upper rock mass sample. A second extrusion block is arranged in the second placement groove, and the second placement groove at one side of the second extrusion block is configured for placing a lower rock mass sample corresponding in position to the upper rock mass sample.

The first extrusion block includes a first small wedge, a first big wedge, and a first adjusting bolt arranged in sequence in the first direction. The first small wedge is located on one side of the first big wedge away from the upper rock mass sample, and a surface joint of the first small wedge and the first big wedge is a first inclined plane. A first through hole communicated with the first placement groove is formed in a side wall of the upper fixed shear box, a first adjusting internal thread hole is formed in a side wall of the first small wedge, and a threaded end of the first adjusting bolt passes through the first through hole and is threaded to the first adjusting internal thread hole.

The second extrusion block includes a second small wedge, a second big wedge, and a second adjusting bolt. The second small wedge is located on one side of the second big wedge away from the lower rock mass sample, and a surface joint of the second small wedge and the second big wedge is a second inclined plane. A second through hole communicated with the second placement groove is formed in a side wall of the lower movable shear box, a second adjusting internal thread hole is formed in a side wall of the second small wedge, and a threaded end of the second adjusting bolt passes through the second through hole and is threaded to the second adjusting internal thread hole.

A first elastic sealing element is arranged on each of one side of the first big wedge close to the upper rock mass sample, one side of the first big wedge close to the lower movable shear box, one side of the second big wedge close to the lower rock mass sample, and one side of the second big wedge close to the upper fixed shear box.

After rotation of the first adjusting bolt, the first adjusting bolt is capable of pulling the first small wedge to move towards a direction close to the first adjusting bolt in the second direction. Through the first inclined plane, the movement of the first small wedge is capable of pushing the first big wedge to move towards one side close to the upper rock mass sample in the first direction and to move towards one side close to the lower movable shear box in the third direction.

After rotation of the second adjusting bolt, the second adjusting bolt is capable of pulling the second small wedge to move towards a direction close to the second adjusting bolt in the second direction. Through the second inclined plane, the movement of the second small wedge is capable of pushing the second big wedge to move towards one side close to the lower rock mass sample in the first direction and to move towards one side close to the upper fixed shear box in the third direction.

An elastic capsule is arranged at each of inner walls of both sides of the first placement groove and the second placement groove in the second direction. The elastic capsule is made of a corrosion-resistant material, and a length of the elastic capsule in the first direction is greater than a length of a corresponding upper rock mass sample or lower rock mass sample. A fluid is able to be injected into the elastic capsule and make the elastic capsule deform elastically with the injection of the fluid.

An upper pressure head device capable of applying a force in the third direction to the upper rock mass sample in the first placement groove is arranged on the upper fixed shear box.

A first communicating channel is arranged in the upper fixed shear box, a second communicating channel is arranged in the lower movable shear box, the first communicating channel and the second communicating channel are located on both sides of an entire of the upper rock mass sample and the lower rock mass sample in the first direction, respectively, and both the first communicating channel and the second communicating channel are communicated with a contact gap between the upper rock mass sample and the lower rock mass sample.

Preferably, the upper fixed shear box includes a fixed shear slider, a first front side plate, and a first rear side plate. The first front side plate and the first rear side plate are arranged in parallel in the second direction. A first U-shaped groove penetrating through the second direction is formed in the fixed shear slider, the first front side plate and the first rear side plate are respectively located on both sides of the first U-shaped groove that the first U-shaped groove penetrates through, a first limiting groove is arranged at each of inner sides of both sides of the first U-shaped groove that the first U-shaped groove penetrates through, and first limiting inner protrusions are arranged at one end of each of the first front side plate and the first rear side plate. Each of the first limiting inner protrusions are respectively clamped into a corresponding first limiting groove. The first limiting groove corresponding to the first front side plate is capable of limiting a movement of the first front side plate away from the first rear side plate in the second direction. The first limiting groove corresponding to the first rear side plate is capable of limiting a movement of the first rear side plate away from the first front side plate in the second direction. The first placement groove is formed jointly by the first front side plate, the first rear side plate and the first U-shaped groove.

The lower movable shear box includes a movable shear slider, a second front side plate, and a second rear side plate. The second front side plate and the second rear side are arranged in parallel in the second direction; a second U-shaped groove penetrating through the second direction is arranged at the movable shear slider, the second front side plate and the second rear side plate are located on both sides of the second U-shaped groove that the second U-shaped groove penetrates through, a second limiting groove is arranged at each of inner sides of both sides of the second U-shaped groove that the second U-shaped groove penetrates through, and second limiting inner protrusions are arranged at one end of each of the second front side plate and the second rear side plate. Each of the second limiting inner protrusions are respectively clamped into a corresponding second limiting groove. The second limiting groove corresponding to the second front side plate is capable of limiting a movement of the second front side plate away from the second rear side plate in the second direction. The second limiting groove corresponding to the second rear side plate is capable of limiting a movement of the second rear side plate away from the second front side plate in the second direction. The second placement groove is formed jointly by the second front side plate, the second rear side plate and the second U-shaped groove.

Preferably, a second elastic sealing element is arranged on each of an inner wall of one side, opposite to the first big wedge, in the first placement groove, and an inner wall of one side, opposite to the second big wedge, in the second placement groove.

Preferably, an accommodating groove is arranged on each of inner walls of both sides of the first placement groove and the second placement groove in the second direction. A lower end of the accommodating groove of the first placement groove on one side is communicated with an upper end of the accommodating groove of the second placement groove on a same side, and an elastic capsule is placed in each accommodating groove. Liquid injection ports communicated with the corresponding elastic capsule are formed in outer walls of both sides of the upper fixed shear box and the lower movable shear box in the second direction, respectively.

Preferably, the inverted U-shaped frame comprises two connecting posts, and a wheel shaft. Lower ends of the two connecting posts are respectively located on two outer side walls of the lower movable shear box in the second direction and are arranged opposite to each other, and upper ends of the two connecting posts are connected by the wheel shaft. Multiple bearings are rotatably arranged on the wheel shaft. A space jointly formed by lower surfaces of each of the bearings, inner sides of the two connecting posts and an upper end surface of the lower movable shear box is configured for the upper fixed shear box to slide in along the first direction.

Preferably, an adjusting mechanism capable of adjusting a position of the wheel shaft in the third direction is arranged on each connecting post.

Preferably, the adjusting mechanism includes a pressure roller block, and a third adjusting bolt. A U-shaped mounting groove with an upward opening is formed in the upper end of each connecting post, and an end portion of the wheel shaft is placed in each U-shaped mounting groove. A pressure roller block is fixedly arranged at the opening of each the U-shaped mounting groove. A threaded hole in threaded connection with the third adjusting bolt is formed in the pressure roller block. A threaded end of the third adjusting bolt is able to pass through the threaded hole and be abutted against the end portion of the wheel shaft in the U-shaped mounting groove.

Preferably, the elastic capsule is made of polytetrafluoroethylene.

A method of using above any one of the shear boxes for testing shear-seepage coupling characteristics of rock mass is further provided in the present disclosure, including the following steps:

Step 1, preparing an upper rock mass sample and a lower rock mass sample, treating a size of each of the upper rock mass sample and the lower rock mass sample as required, and ensuring that surfaces of the upper rock mass sample and the lower rock mass sample are clean;

Step 2, placing the upper rock mass sample in a first placement groove of an upper fixed shear box, mounting a first extrusion block on one side of the upper rock mass sample to ensure that a position of the upper rock mass sample is stable; similarly, placing the lower rock mass sample in a second placement groove of a lower movable shear box, and mounting a second extrusion block; and mounting a first sealing element and an elastic capsule at corresponding positions;

Step 3, mounting a connection limiting part on the lower movable shear box, and sliding the upper fixed shear box into each inverted U-shaped frame above the lower movable shear box in a first direction; and Step 4, placing an entire shear box assembled in Step 3 on a test bench, and adjusting a position of the shear box to ensure stability, enabling a first communicating channel and a second communicating channel to communicate with a water pressure system, and applying a required pressure to the upper rock mass sample through an upper pressure head device, thus starting a test.

Compared with the prior art, the present disclosure has the following technical effects:

According to the shear box for testing shear-seepage coupling characteristics of rock mass provided by the present disclosure, a first extrusion block arranged in a first placement groove and a second extrusion block arranged in a second placement groove are configured to extrude an upper rock mass sample and a lower rock mass sample, respectively. For example, the extrusion of the first extrusion block is as follows: utilizing the integrated action of the first adjusting bolt and the first inclined plane between the first small wedge and a first big wedge, and through the movement of the first small wedge pulled in the second direction by the first adjusting bolt, and through the first inclined plane, the movement of the first small wedge in the second direction pushes the first big wedge to achieve movements in two directions, that is, the first big wedge moves towards a direction close to the upper rock mass sample in the first direction to extrude a first elastic sealing element on this side, and moves towards a direction close to the lower movable shear box in the third direction to extrude a first elastic sealing element on this side. The first extrusion block and the second extrusion block can finally achieve the extrusion sealing of the first elastic sealing elements on the corresponding first big wedge and the second big wedge, respectively, thus ensuring the extrusion sealing effect of the upper rock mass sample in the first direction and the lower rock mass sample in the third direction. For the sealing on both sides of the upper rock mass sample and the lower rock mass sample in the second direction, by means of the method of arranging the elastic capsule, and injecting the fluid into the elastic capsule, the elastic capsule 50 is expanded and elastically deformed, thus sealing the joints of the corresponding upper rock mass sample and lower rock mass sample and gaps around the elastic capsule to form multiple sealing guarantees. Moreover, the elastic capsule is made of a corrosion-resistant material, which may have a certain corrosion resistance to the injected fluid, finally providing strong sealing and corrosion resistance for the direct shear test system of the rock mass under seepage conditions.

Further, through the cooperation of the first limiting inner protrusion arranged on each of the first front side plate and the first rear side plate with the first limiting groove arranged on the fixed shear slider, the first front side plate and the first rear side plate are disengaged outwards. Compared with the traditional connection mode of connecting the first front side plate and the first rear side plate to the fixed shear slider by bolts, the structure is simple, and the mounting is more convenient and firmer.

Further, the second elastic sealing element is provided to seal the upper rock mass sample and the lower rock mass sample better, thus improving the sealing effect.

Further, the accommodating groove can accommodate the elastic capsule, making the elastic capsule have a certain accommodating space to accommodate a certain amount of fluid. The connecting arrangement of the accommodating grooves on the same side enables the upper and lower elastic capsules on the same side to make contact with each other when expanding. Through the mutual contact and extrusion of the two elastic capsules, the sealing at the surface joint is achieved. The provided liquid injection port is convenient for injecting fluid into the elastic capsule.

Further, an inverted U-shaped frame is provided to ensure the connection firmness between the upper fixed shear box and the lower movable shear box in a third direction. A wheel shaft and a bearing are provided to make the upper fixed shear box form rolling friction when sliding into a gap between the wheel shaft and the lower movable shear box, thus reducing the friction resistance.

Further, the adjusting mechanism is provided to achieve the position adjusting of the wheel shaft in the third direction, thus achieving tight extrusion between the upper fixed shear box and the lower movable shear box, and achieving the sealing effect at the joint of the upper fixed shear box and the lower movable shear box.

Further, the adjusting mechanism adopts an arrangement of a pressure roller block and a U-shaped mounting groove, and a third adjusting bolt is used to extrude an end portion of the wheel shaft. The adjusting mechanism is simple in structure, convenient to adjust, stable, and reliable.

Further, the polytetrafluoroethylene material is corrosion-resistant and wear-resistant, and has a small friction coefficient, which can resist the corrosiveness of an acidic environment such as carbon dioxide solution.

BRIEF DESCRIPTION OF THE DRAWINGS

To describe the technical solutions of the embodiments of the present disclosure or in the prior art more clearly, the following briefly introduces the accompanying drawings required in the embodiments. Apparently, the accompanying drawings in the following description show merely some embodiments of the present disclosure, and those skilled in the art may still derive other drawings in accordance with these accompanying drawings without creative efforts.

Figure 1:
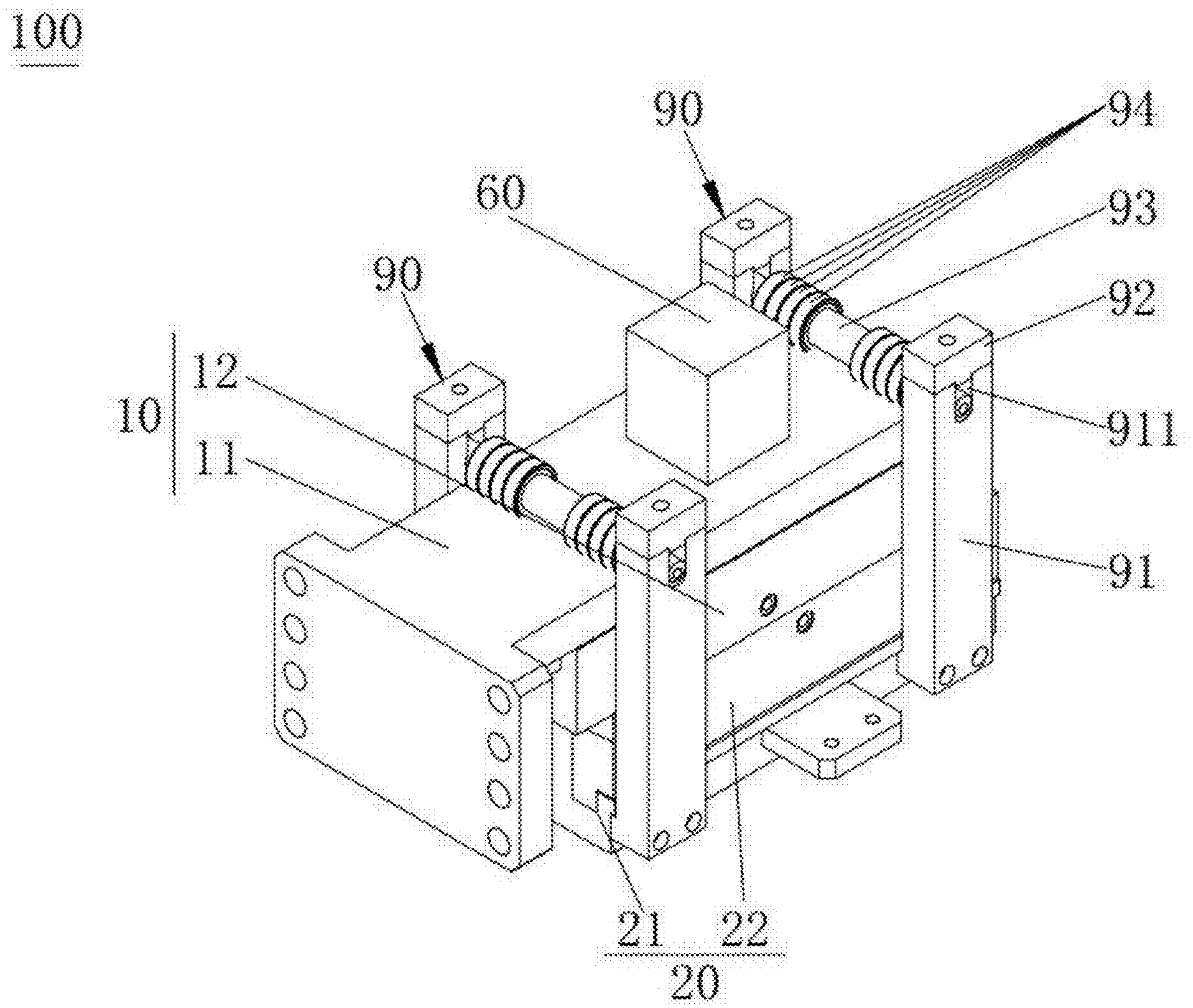
FIG. 1 is a schematic view of an overall structure of a shear box for testing shear-seepage coupling characteristics of rock mass according to the present disclosure.

Reference signs in the drawings: 100, shear box for testing shear-seepage coupling characteristics of rock mass;

10, upper fixed shear box; 11, fixed shear slider; 111, first communicating channel; 12, first front side plate; 121, first limiting inner protrusion; 13, first rear side plate; 14, first extrusion block; 141, first small wedge; 142, first big wedge; 143, first inclined plane; 15, first adjusting bolt;

20, lower movable shear box; 21, movable shear slider; 211, second communicating channel; 22, second front side plate; 221, second limiting inner protrusion; 23, second rear side plate; 24, second extrusion block; 241, second small wedge; 242, second big wedge; 243, second inclined plane; 25, second adjusting bolt;

30, upper rock mass sample;

40, lower rock mass sample;

50, elastic capsule; 51, liquid injection port;

60, upper pressure head device;

70, first elastic sealing element;

80, second elastic sealing element;

90, inverted U-shaped frame; 91, connecting post; 911, U-shaped mounting groove; 92, pressure roller block; 93, wheel shaft; 94, bearing.

DETAILED DESCRIPTION OF THE EMBODIMENTS

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by those skilled in the art based on the embodiments of the present disclosure without creative efforts shall fall within the protection scope of the present disclosure.

An objective of the present disclosure is to provide a shear box for testing shear-seepage coupling characteristics of rock mass and a method of using the shear box, so as to solve the problems in the prior art, and to provide strong sealing and corrosion resistance for a direct shear test system of the rock mass under a seepage condition.

In order to make the above-mentioned objectives, features and advantages of the present disclosure more clearly, the present disclosure is further described in detail below with reference to the accompanying drawings and the implementations.

Embodiment I

A shear box 100 for testing shear-seepage coupling characteristics of rock mass is provided in this embodiment, which is mainly used to, but not limited to, test the shear-$ScCO_2$ seepage coupling characteristics of rock mass. As shown in FIG. 1 to FIG. 8, the shear box includes an upper fixed shear box 10, a lower movable shear box 20, and a connection limiting part.

A length direction of the upper fixed shear box 10 is taken as a first direction, a width direction of the upper fixed shear box 10 is taken as a second direction, the first direction is perpendicular to the second direction, and a third direction is perpendicular to both the first direction and the second direction.

The connection limiting part includes two inverted U-shaped frames 90, and each of the two inverted U-shaped frames is arranged in sequence in the first direction, and both ends of the bottom of each inverted U-shaped frame 90 are fixed to both sides of the lower movable shear box 20, respectively. The lower movable shear box 20 is located below the upper fixed shear box 10, one end of the upper fixed shear box 10 can slide in the first direction into each of the inverted U-shaped frames 90 above the lower movable shear box 20.

A first placement groove with a downward opening is arranged at the upper fixed shear box 10, and a second placement groove with an upward opening is arranged at the lower movable shear box 20. The opening of the first placement groove is communicated with the opening of the second placement groove. A first extrusion block 14 is arranged in the first placement groove, and the first placement groove at one side of the first extrusion block 14 is used for placing an upper rock mass sample 30. A second extrusion block 24 is arranged in the second placement groove, and the second placement groove at one side of the second extrusion block 24 is used for placing a lower rock mass sample 40 corresponding to the upper rock mass sample 30.

The first extrusion block 14 includes a first small wedge 141, a first big wedge 142, and a first adjusting bolt 15 arranged in sequence in the first direction. The first small wedge 141 is located on one side of the first big wedge 142 away from the upper rock mass sample 30, and a surface joint of the first small wedge 141 and the first big wedge 142 is a first inclined plane 143. A first through hole communicated with the first placement groove is formed in a side wall of the upper fixed shear box 10, a first adjusting internal thread hole is formed in a side wall of the first small wedge 141, and a threaded end of the first adjusting bolt 15 is threaded to the first adjusting internal thread hole by passing through the first through hole.

The second extrusion block 24 includes a second small wedge 241, a second big wedge 242 and a second adjusting bolt 25. The second small wedge 241 is located on one side of the second big wedge 242 away from the lower rock mass sample 40, and a surface joint of the second small wedge 241 and the second big wedge 242 is a second inclined plane 243. A second through hole communicated with the second placement groove is formed in a side wall of the lower movable shear box 20, a second adjusting internal thread hole is formed in a side wall of the second small wedge 241, and a threaded end of the second adjusting bolt 25 is threaded to the second adjusting internal thread hole by passing through the second through hole.

A first elastic sealing element 70 is arranged on each of one side of the first big wedge 142 close to the upper rock mass sample 30, one side of the first big wedge 142 close to the lower movable shear box 20, one side of the second big wedge 242 close to the lower rock mass sample 40, and one side of the second big wedge 242 close to the upper fixed shear box 10.

After rotation of the first adjusting bolt 15, the first small wedge 141 can be pulled by the first adjusting bolt 15 to move towards a direction close to the first adjusting bolt 15 in the second direction. Through the first inclined plane 143, the first big wedge 142 can be pushed by means of the movement of the first small wedge 141 to move towards one side close to the upper rock mass sample 30 in the first direction and to move towards one side close to the lower movable shear box 20 in the third direction.

After rotation of the second adjusting bolt 25, the second small wedge 241 can be pushed by the second adjusting bolt 25 to move towards a direction close to the second adjusting bolt 25 in the second direction. Through the second inclined plane 243, the second big wedge 242 can be pushed be means of the movement of the second small wedge 241 to move towards one side close to the lower rock mass sample 40 in the first direction and to move towards one side close to the upper fixed shear box 10 in the third direction.

An elastic capsule 50 is arranged on each of inner walls of both sides of the first placement groove and the second placement groove in the second direction. The elastic capsule 50 is made of a corrosion-resistant material, and a length of the elastic capsule 50 in the first direction is greater than that of the corresponding upper rock mass sample 30 or lower rock mass sample 40. Fluid can be injected into the elastic capsule 50 and make the elastic capsule 50 deform elastically with the injection of the fluid.

An upper pressure head device 60 capable of applying a force in the third direction to the upper rock mass sample 30 in the first placement groove is arranged on the upper fixed shear box 10.

A first communicating channel 111 is arranged in the upper fixed shear box 10, and a second communicating channel 211 is arranged in the lower movable shear box 20. The first communicating channel 111 and the second communicating channel 211 are respectively located on both sides of the entire of the upper rock mass sample 30 and the lower rock mass sample 40 in the first direction, and both the first communicating channel 111 and the second communicating channel 211 are communicated with a contact gap between the upper rock mass sample 30 and the lower rock mass sample 40.

The first extrusion block 14 arranged in the first placement groove and the second extrusion block 24 arranged in the second placement groove are used to extrude the upper rock mass sample 30 and the lower rock mass sample 40, respectively. For example, the extrusion of the first extrusion block 14 is as follows: utilizing the integrated action of the first adjusting bolt 15 and the first inclined plane 143 between the first small wedge 141 and the first big wedge 142, and through the movement of the first small wedge 141 pulled in the second direction by the first adjusting bolt 15, and through the first inclined plane 143, the movement of the first small wedge 141 in the second direction pushes the first big wedge 142 to achieve movements in two directions, that is, the first big wedge 142 moves towards a direction close to the upper rock mass sample 30 in the first direction to extrude the first elastic sealing element 70 on this side, and moves towards a direction close to the lower movable shear box 20 in the third direction to extrude the first elastic sealing element 70 on this side. The first extrusion block 14 and the second extrusion block 24 can finally achieve the extrusion sealing of the first elastic sealing elements 70 on the corresponding first big wedge 142 and the second big wedge 242, respectively, thus ensuring the extrusion sealing effect of the upper rock mass sample 30 in the first direction and the lower rock mass sample 40 in the third direction. For the sealing on both sides of the upper rock mass sample 30 and the lower rock mass sample 40 in the second direction, by means of the method of arranging the elastic capsule 50, and injecting the fluid into the elastic capsule 50, the elastic capsule 50 is expanded and elastically deformed, thus sealing the joints of the corresponding upper rock mass sample 30 and lower rock mass sample 40 and gaps around the elastic capsule 50 to form multiple sealing guarantees. Moreover, the elastic capsule 50 is made of a corrosion-resistant material, which may have a certain corrosion resistance to the injected fluid, finally providing strong sealing and corrosion resistance for the direct shear test system of the rock mass under seepage conditions.

Specifically, when the fluid is injected through the first communicating channel 111 and the second communicating channel 211, methods of injecting the fluid are suitable for various types, such as unidirectional injection, bidirectional injection, continuous injection, pulse injection and automatic injection in common. Testers can adjust a rate and pressure of the injected fluid through an accurate injection system, thus controlling the internal mixing effect, and preventing the generation of bubbles and foams from affecting the test effect. Meanwhile, the magnitude and intensity of a shearing force applied to the sample can be adjusted to maintain the stability of the test conditions, thus satisfying the requirements of different tests for shearing, mixing effect and stability.

Specifically, the extrusion principle of the first extrusion block 14 is the same as that of the second extrusion block 24. The first extrusion block 14 is taken as an example for specific description, as shown in FIG. 5 to FIG. 8.

Specifically, a first adjusting bolt 15 is arranged on the first small wedge 141, and the first adjusting bolt 15 is arranged perpendicular to a side wall of the first small wedge block 141. A corresponding first adjusting internal thread hole is formed within the first small wedge 141. A pressure acting on an interaction surface (i.e., a first inclined plane 143) of the first small wedge 141 and the first bid wedge 142 is produced by tightening the first adjusting bolt 15 on the first small wedge 141. The first small wedge 141 can move in the second direction, and the movement of the first small wedge 141 in the second direction can simultaneously provide driving forces in two directions for the first large wedge 142 through the action of the first inclined surface 143: one of the driving forces is that the first small wedge 141 can extrude the first big wedge 142 in the first direction through the first inclined plane 143 to drive the first big wedge 142 to move towards a direction close to the upper rock mass sample 30; and the other one of the driving forces is that the first small wedge 141 can extrude the first big wedge 142 in the third direction through the first inclined plane 143 to drive the first big wedge 142 to move towards a direction close to the lower movable shear box 20. That is, the movement of the first small wedge 141 in the second direction makes the first big wedge 142 to move in the first direction and the third direction through the first inclined plane 143, thus achieving the extrusion and sealing for the upper rock mass sample 30 by extruding the first elastic element 70 on the corresponding side.

Specific structural components of the upper fixed shear box 10 and the lower movable shear box 20 are as follows:

In an alternative solution of this embodiment, preferably, as shown in FIG. 1 to FIG. 4, the upper fixed shear box 10 includes a fixed shear slider 11, a first front side plate 12, and a first rear side plate 13. The first front side plate 12 and the first rear side plate 13 are arranged in parallel in the second direction. A first U-shaped groove penetrating through the second direction is arranged at the fixed shear slider 11, the first front side plate 12 and the first rear side plate 13 are respectively located on both sides of the first U-shaped groove that the first U-shaped groove penetrates through, a first limiting groove is arranged at each of inner sides of both sides of the first U-shaped groove that the first U-shaped groove penetrates through, and first limiting inner protrusions 121 are arranged at one end of each of the first front side plate 12 and the first rear side plate 13. Each of the first limiting inner protrusions 121 are respectively clamped into a corresponding first limiting groove. The first limiting groove corresponding to the first front side plate 12 can limit the movement of the first front side plate 12 away from the first rear side plate 13 in the second direction. The first limiting groove corresponding to the first rear side plate 13 can limit the first rear side plate 13 from moving towards a direction away from the first front side plate 12 in the second direction. The first placement groove is formed jointly by the first front side plate 12, the first rear side plate 13 and the first U-shaped groove.

The lower movable shear box 20 includes a movable shear slider 21, a second front side plate 22, and a second rear side plate 23. The second front side plate 22 and the second rear side plate 23 are arranged in parallel in the second direction. A second U-shaped groove penetrating through the second direction is arranged at the movable shear slider 21, the second front side plate 22 and the second rear side plate 23 are located on both sides of the second U-shaped groove that the second U-shaped groove penetrates through, a second limiting groove is arranged at each of inner sides of both sides of the second U-shaped groove that the second U-shaped groove penetrates through, and second limiting inner protrusions 221 are arranged at one end of each of the second front side plate 22 and the second rear side plate 23. Each of the second limiting inner protrusions 221 are respectively clamped into a corresponding second limiting groove. The second limiting groove corresponding to the second front side plate 22 can limit the movement of the second front side plate 22 away from the second rear side plate 23 in the second direction. The second limiting groove corresponding to the second rear side plate 23 can limit the movement of the second rear side plate 23 away from the second front side plate 22 in the second direction. The second placement groove is formed jointly by the second front side plate 22, the second rear side plate 23 and the second U-shaped groove.

Through the cooperation of the first limiting inner protrusion 121 arranged on each of the first front side plate 12 and the first rear side plate 13 with the first limiting groove arranged on the fixed shear slider 11, the first front side plate 12 and the first rear side plate 13 are disengaged outwards. Compared with the traditional connection mode of connecting the first front side plate 12 and the first rear side plate 13 to the fixed shear slider 1 by bolts, no excessive bolt members are involved, seepage paths are relatively few, the structure is simple, and the mounting is more convenient and firmer.

Specifically, a connecting plate configured for connecting to a host frame is arranged at one end of the fixed shear slider 11. Multiple fixed connecting holes are formed in the connecting plate. Specifically, the connecting plate and the fixed shear slider 11 are integrally formed.

Specifically, an extrusion of the elastic capsule 50 on the first front side plate 12 is taken as an example. As the elastic capsule 50 is elastically deformed after the fluid is injected into the elastic capsule 50, a pressure in the second direction is generated to extrude the first front side plate 12. Due to the cooperative structure effect of the first limiting inner protrusion 121 on the first front side plate 12 and the first limiting groove of the fixed shear slider 11, the first front side plate 12 and the fixed shear slider 11 can be mutually spliced and extruded to transfer the force. Therefore, the first front side plate 12 is subjected to pressure and tends to move outwards, and the first limiting groove of the fixed shear slider 11 plays a role of blocking the outward movement of the first front side plate 12. Therefore, the pressure exerted on the first front side plate 12 is transferred outwards to the fixed shear slider 11, and the fixed shear slider 11 also tends to move outwards after subjected to the pressure. Since each of connecting posts 91 is a fixed structure and can generate an inward reaction force to block the fixed shear slider 11, and meanwhile, each of the connecting posts 91 is subjected to an outward pressure, the outward pressure is transferred to each of the connecting posts 91 by the fixed shear slider 11, the connecting posts 91 play a role of blocking the outward movement of the fixed shear slider 11, and generates an inward reaction force to the fixed shear slider 11, thus achieving the effect of tightly extruding various members, and achieving an effective sealing at the joint of the first front side plate 12, the fixed shear slider 11 and the connecting posts 91.

Figure 2:
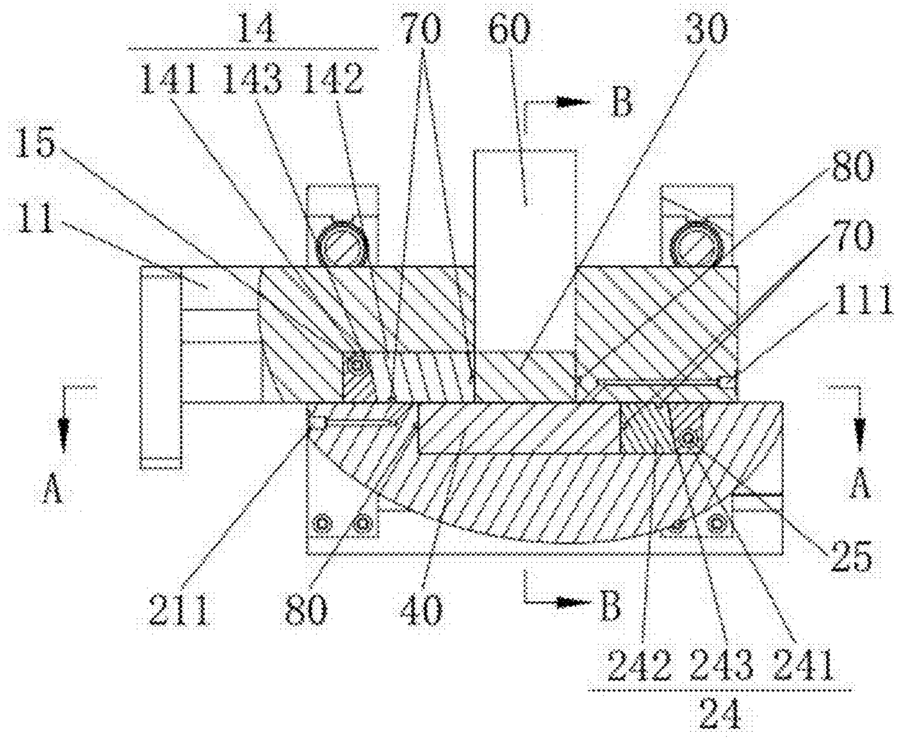
FIG. 2 is a schematic view of an internal structure of a shear box for testing shear-seepage coupling characteristics of rock mass according to the present disclosure.

For a sealing structure:

In an alternative solution of the embodiment, preferably, as shown in FIG. 2, a second elastic sealing element 80 is arranged on each of an inner wall of one side, opposite to the first big wedge 142, in the first placement groove, and an inner wall of one side, opposite to the second big wedge 242, in the second placement groove. The second elastic sealing element 80 is provided to seal the upper rock mass sample 30 and the lower rock mass sample 40 better, thus improving the sealing effect.

Specifically, both the first elastic sealing element 70 and the second elastic sealing element 80 may be made of a sealing rubber pad.

Specifically, the sealing rubber pas has four effects:

First, leakage prevention: the sealing rubber pad can effectively prevent internal gas or liquid thereof from leaking, which is crucial for maintaining specific environmental conditions, or keeping stability of a test system.

Second, pollution prevention: the sealing rubber pad can also prevent foreign impurities from entering the test system, thus keeping the purity of a test environment. In some tests with high requirements for the test condition, any external pollutants may have adverse effects on the test result, so the external environment can be effectively isolated by using the sealing rubber pad.

Third, friction and wear reduction: in some components needing to be disassembled and assembled frequently, the sealing rubber pad can reduce the friction and wear between the components, which is conducive to the lone-term stable operation and lifetime prolongation of the equipment.

Fourth, insulation and heat insulation: the sealing rubber pad generally has a certain performance of insulation and thermal insulation, which can play a role in some test conditions that require insulation or thermal insulation.

A structure about the connection limiting part is introduced as follows:

In an alternative solution of this embodiment, preferably, as shown in FIG. 1 to FIG. 4, the inverted U-shaped frame 90 includes two connecting posts 91, and a wheel shaft 93. Lower ends of the two connecting posts 91 are respectively located on two outer side walls of the lower movable shear box 20 in the second direction and are arranged opposite to each other, and upper ends of the two connecting posts 91 are connected by the wheel shaft 93. Multiple bearings 94 are rotatably arranged on the wheel shaft 93. A space jointly formed by lower surfaces of each of the bearings 94, inner sides of the two connecting posts 91 and an upper end surface of the lower movable shear box 20 is used for the upper fixed shear box 10 to slide in along the first direction. The inverted U-shaped frame 90 is provided to ensure the connection firmness between the upper fixed shear box 10 and the lower movable shear box 20 in the third direction. The wheel shaft 93 and the bearings 94 are provided to make the upper fixed shear box 10 form rolling friction when sliding into a gap between the wheel shaft 93 and the lower movable shear box 20, thus reducing the friction resistance.

Specifically, the bearing 94 is chosen as a deep groove ball bearing 94. As shown in FIG. 1, eight bearings 94 is arranged on each wheel shaft 93, and every four bearings 94 are next to each other.

In an alternative solution of this embodiment, preferably, as shown in FIG. 1 to FIG. 4, an adjusting mechanism capable of adjusting a position of the wheel shaft 93 in the third direction is arranged on each connecting post 91. The adjusting mechanism is provided to achieve the position adjusting of the wheel shaft 93 in the third direction, thus achieving tight extrusion between the upper fixed shear box 10 and the lower movable shear box 20, and achieving the sealing effect at the joint of the upper fixed shear box 10 and the lower movable shear box 20.

In an alternative solution of this embodiment, preferably, as shown in FIG. 1 to FIG. 4, the adjusting mechanism includes a pressure roller block 92, and a third adjusting bolt. A U-shaped mounting groove 911 with an upward opening is formed in the upper end of each connecting post 91, and an end portion of the wheel shaft 93 is placed in each U-shaped mounting groove 911. A pressure roller block 92 is fixedly arranged at the opening of each the U-shaped mounting groove 911. A threaded hole in threaded connection with the third adjusting bolt is formed in the pressure roller block 92; and a threaded end of the third adjusting bolt can pass through the threaded hole and be abutted against the end portion of the wheel shaft 93 in the U-shaped mounting groove 911. The adjusting mechanism adopts an arrangement of the pressure roller block 92 and the U-shaped mounting groove 911, and the third adjusting bolt is used to extrude the end portion of the wheel shaft 93. The adjusting mechanism is simple in structure, convenient to adjust, stable, and reliable.

Figure 3:
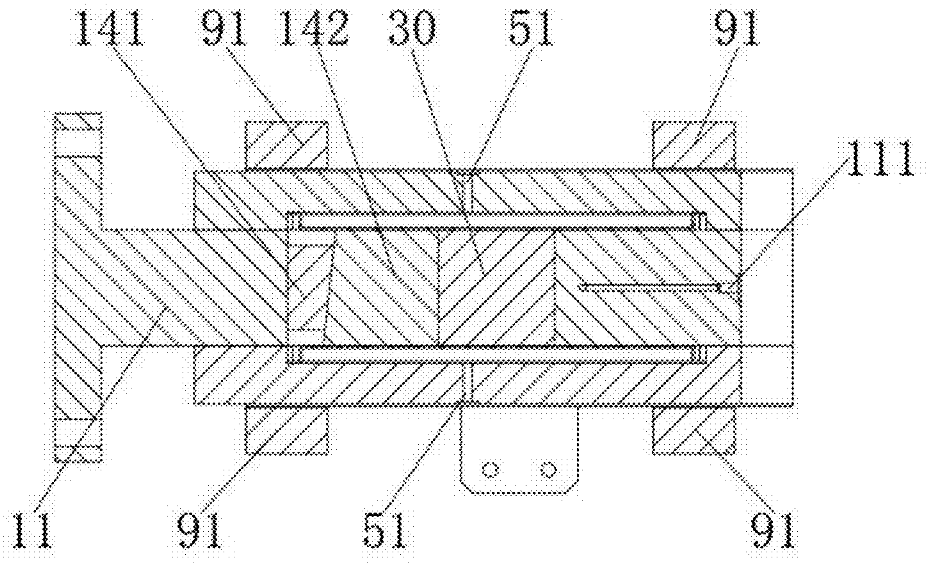
FIG. 3 is a sectional view cut along A-A direction in FIG. 2.
Figure 4:
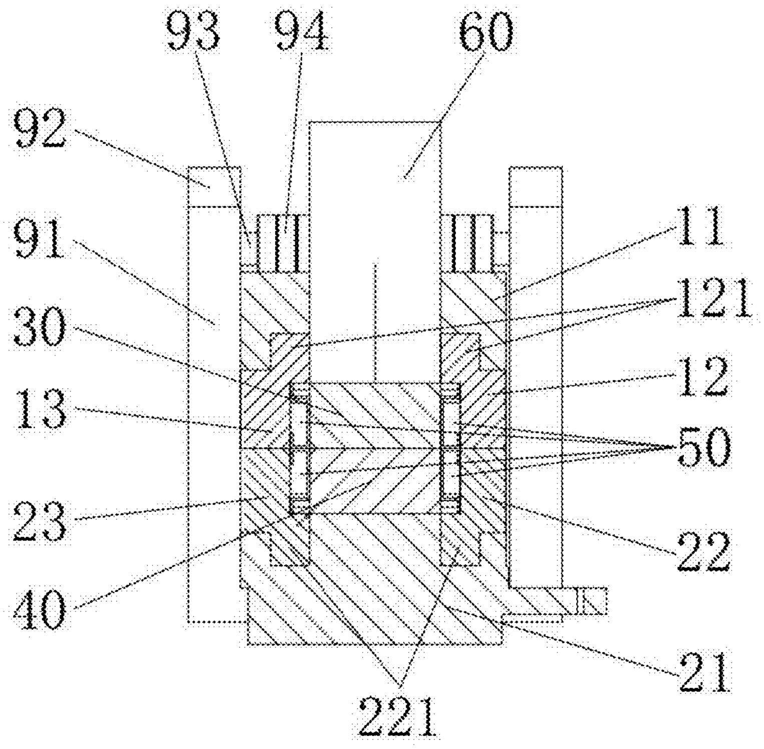
FIG. 4 is a sectional view cut along B-B direction in FIG. 2.
Figure 5:
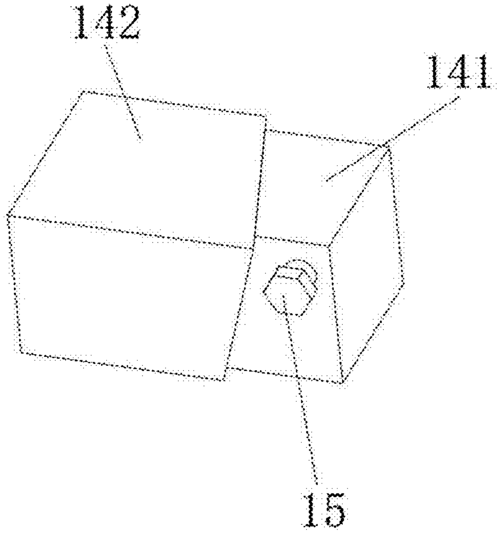
FIG. 5 is a schematic diagram of an extrusion structure of a first extrusion block in a shear box for testing shear-seepage coupling characteristics of rock mass according to the present disclosure.
Figure 6:
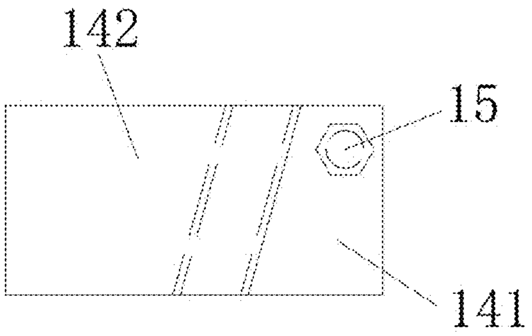
FIG. 6 is a front view of FIG. 5.
Figure 7:
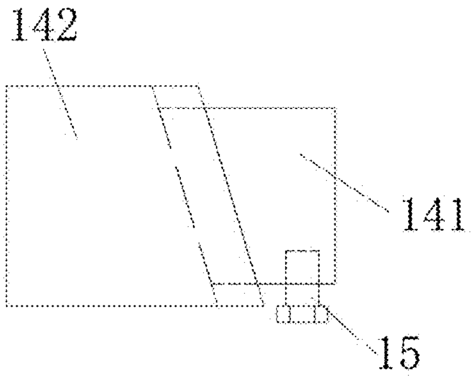
FIG. 7 is a top view of FIG. 5.
Figure 8:
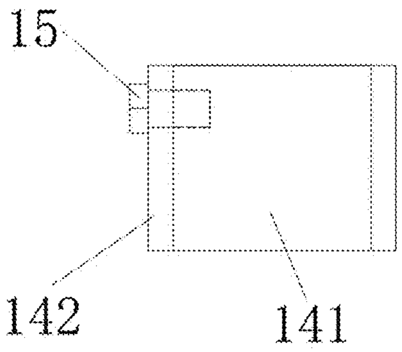
FIG. 8 is a right view of FIG. 5.

The elastic capsule 50 is introduced as follows:

In an alternative solution of this embodiment, preferably, as shown in FIG. 3 to FIG. 4, an accommodating groove is arranged on each of inner walls of both sides of the first placement groove and the second placement groove in the second direction. A lower end of the accommodating groove of the first placement groove on one side is communicated with an upper end of the accommodating groove of the second placement groove on the same side. An elastic capsule 50 is placed in each accommodating groove. Liquid injection ports 51 communicated with the corresponding elastic capsule 50 are formed in outer walls of both sides of the upper fixed shear box 10 and the lower movable shear box 20 in the second direction, respectively. The accommodating groove can accommodate the elastic capsule 50, making the elastic capsule have a certain accommodating space to accommodate a certain amount of fluid. The connecting arrangement of the accommodating grooves on the same side enables the upper and lower elastic capsules 50 on the same side to make contact with each other when expanding. Through the mutual contact and extrusion of the two elastic capsules 50, the sealing at the surface joint is achieved (although a pressure is generated by the mutual extrusion between the two elastic capsules 50, the friction coefficient of the elastic capsules is small, so the extrusion between the two elastic capsules 50 does not influence a test value of shear resistance in the shear test process of the rock mass, thus ensuring the test accuracy). The provided liquid injection port 51 is convenient for injecting fluid into the elastic capsule 50.

Specifically, the accommodating groove is formed on each of the first front side plate 12, the first rear side plate 13, the second front side plate 22, and the second rear side plate 23.

In an alternative solution of this embodiment, preferably, the elastic capsule 50 is made of polytetrafluoroethylene. The polytetrafluoroethylene material is corrosion-resistant and wear-resistant, and has a small friction coefficient, which can resist the corrosiveness of an acidic environment such as carbon dioxide solution.

Specifically, the elastic capsule 50 is of a hollow structure, sealing liquid, such as water and other liquid which have no special property and cannot affect the stability of the test, can be injected into an inner of the elastic capsule 50.

Specifically, the elastic capsule 50 can cover the side wall areas of corresponding upper rock mass sample 30 and lower rock mass sample 40. Alternatively, the elastic capsule 50 can cover the largest side wall area of the upper rock mass sample 30 and the lower rock mass sample 40, thus ensuring a better sealing effect on the whole.

Specifically, with the fluid injected into the inner of the elastic capsule 50, an outer wall of the elastic capsule 50 is gradually expanded due to the extrusion of the internal fluid to generate pressure on its surrounding surface, and the outer wall of the elastic capsule 50 is expanded in the direction of the upper rock mass sample 30 or the lower rock mass sample 40 and the surrounding area thereof, thus achieving the effect of extruding a contact surface in contact with the outer wall of the elastic capsule 50. The expansion property of the elastic capsule 50 can provide multiple sealing guarantees: firstly, the elastic capsule 50 is expanded in the direction of the upper rock mass sample 30 or the lower rock mass sample 40 to ensure the sealing of contact with the sample; and secondly, the expansion of the elastic capsule 50 in the direction away from the upper rock mass sample 30 or the lower rock mass sample 40 can make it form a sealing layer with a side wall of the opposite side. The functions of the above multiple sealing guarantees ensure the reliability and accuracy of the test results. Meanwhile, the excellent corrosion resistance of the elastic capsule can ensure the full play of the corrosion resistance, and further meet the requirements of long-period tests, thus avoiding the disadvantages of frequent maintenance or replacement of the shear box, and ensuring the reliability and accuracy of test results.

Embodiment II

A using method (sample loading, the whole sealing process and the test flow thereof) based on the shear box for testing shear-seepage coupling characteristics of rock mass in Embodiment I is provided in this embodiment, including the following steps:

Step 1, an upper rock mass sample and a lower rock mass sample are prepared, and the size of the upper rock mass sample and the lower rock mass sample is treated as required, and it is ensured that surfaces of the upper rock mass sample and the lower rock mass sample are clean.

Step 2, the upper rock mass sample is placed in a first placement groove of an upper fixed shear box, a first extrusion block is mounted on one side of the upper rock mass sample to ensure that a position of the upper rock mass sample is stable. Similarly, the lower rock mass sample is placed in a second placement groove of a lower movable shear box, and a second extrusion block is mounted. A first sealing element and an elastic capsule are mounted at corresponding positions.

Step 3, a connection limiting part is mounted on the lower movable shear box, and the upper fixed shear box is slid along a first direction into each inverted U-shaped frame above the lower movable shear box.

Step 4, an entire shear box assembled in Step 3 is placed on a test bench, and a position of the shear box is adjusted to ensure stability. A first communicating channel and a second communicating channel are communicated with a water pressure system (one end serving as a water inlet channel is connected to a plunger type metering pump capable of providing stable high permeability water pressure, and one end serving as a water outlet channel is connected to a micro seepage servo control system), and a required pressure is applied to the upper rock mass sample through an upper pressure head device to start the test.

Specifically, prior to Step 1, it is ensured that the structures of the upper fixed shear box, the lower movable shear box and the connection limiting part are intact and cleaned.

Specifically, in Step 2, a second sealing element is mounted at a corresponding position to ensure tight attachment at each position.

Specifically, in Step 2, it is ensured that a length of the elastic capsule is greater than that of a corresponding sample, thus providing effective sealing.

Specifically, in Step 3, the adjusting mechanism can be adjusted gradually to achieve tight connection between the upper and lower shear boxes, thus ensuring that there is no gap at each joint.

Specifically, after Step 3, each sealing position is checked to ensure that the first sealing element, the second sealing element and the elastic capsule are located at correct positions without being damaged or displacing. If necessary, the connection limiting part can be adjusted again to ensure an optimal sealing effect. The sealing is verified: a certain pressure is applied, the states of the first sealing element, the second sealing element and the elastic capsule before and after the tests are compared to verify whether the sealing performance meets the expectation or not.

Specifically, in Step 4, the required pressure is applied to the upper rock mass sample by the upper pressure head device to ensure that the test conditions meet expected requirements. Test starting: test equipment is started, and test data is started to record, including related parameters such as shear stress and seepage rate of the rock mass. Sealing condition monitoring: the sealing condition is continuously monitored in the test process, and special attention is paid to the state of the elastic capsule to ensure the sealing performance. Data recording: data in the test process are recorded, including test time, applied force or pressure, deformation of the rock mass sample, and the like. Test ending: after the test is completed, the rock mass sample is unloaded, the data are sorted and analyzed to acquire related results of the shear-seepage coupling characteristics of the rock mass.

Embodiment III

The description of related flows of other related tests based on the shear box for testing the coupling characteristics of shear-seepage of rock mass in Embodiment I is provided in this embodiment.

Strong sealing and corrosion resistance are provided for a direct shear test system of rock mass under a seepage condition. The flows of testing and monitoring seepage parameters and mechanical parameters include the following steps.

Step 1, equipment inspection: it is checked that whether various components of the shear box for testing shear-seepage coupling characteristics of rock mass are intact or not, and the components include an upper fixed shear box, a lower movable shear box, and a connection limiting part, and the like. Seepage monitoring equipment (e.g., a velocimeter, a thermometer, a manometer, etc.) and mechanical parameter testing equipment (e.g., a force sensor and a deformation sensor, etc.) should be ready and in normal working condition.

Step 2, sample preparation: a rock mass sample is prepared according to test demands, and the size of the sample is treated as required. Necessary treatment shall be carried out on a surface of the rock mass sample to ensure that the surface is smooth and clean, and convenient to closely contact with the corresponding shear box to form a good seal.

Step 3, seepage parameter testing

Fluid preparation: A fluid for seepage testing is prepared, an appropriate fluid type and concentration are selected according to the test demands, and a temperature and pressure of the fluid are adjusted according to the test requirements.

Flow velocity monitoring: A velocimeter or a liquid flow rate monitoring device is connected to a communicating channel of the shear box and the connection is ensured to be firm. Flow velocity monitoring equipment is started to record the flow velocity changes of the fluid during the test, including the stability of the flow velocity, and the change trend of the flow velocity, and the like.

Fluid temperature and seepage pressure monitoring: when the fluid flows through the shear box, a thermometer, a pressure gauge or a pressure sensor is used to monitor a fluid temperature and a seepage pressure. The data of the fluid temperature and the seepage pressure are recorded in different time periods, so as to later analyze a seepage behavior and the relationship between the seepage behavior and the mechanical parameters.

Step 4, seepage parameter testing

Force or pressure monitoring: the test equipment is used to apply the required force or pressure, and a force sensor and other equipment are used to monitor and record the force or pressure changes of the rock mass sample.

Deformation monitoring: in the test process, the deformation of the rock mass sample is monitored using a deformation sensor and other measurement tools. The deformation data is recorded in real time, and the deformation response of the rock mass sample is analyzed as required.

Step 5, data saving

The accuracy and integrity of the data record are ensured, and the record is saved in time. The data recorded in the test process are filed and stored for subsequent reference and analysis.

Specific examples are used herein for illustration of the principles and embodiments of the present disclosure. The description of the above embodiments is merely used to help understand the method and its core ideas of the present disclosure. In addition, those skilled in the art can make changes in terms of specific embodiments and application scope in accordance with the ideas of the present disclosure.

In conclusion, the content of this specification shall not be construed as a limitation to the present disclosure.

What is claimed is:

1. A shear box for testing shear-seepage coupling characteristics of rock mass, comprising:

an upper fixed shear box, a length direction of the upper fixed shear box is taken as a first direction, a width direction of the upper fixed shear box is taken as a second direction, the first direction is perpendicular to the second direction, and a third direction is perpendicular to both the first direction and the second direction a lower movable shear box, and a connection limiting part, the connection limiting part comprises two inverted U-shaped frames, and the two inverted U-shaped frames are arranged in sequence in the first direction, and both ends of a bottom of each of the two Inverted U-shaped frames are fixed to both sides of the lower movable shear box, respectively;

the lower movable shear box is located below the upper fixed shear box, one end of the upper fixed shear box is capable of sliding into the inverted U-shaped frame above the lower movable shear box in the first direction;

a first placement groove with a downward opening is arranged in the upper fixed shear box, and a second placement groove with an upward opening is arranged in the lower movable shear box;

the downward opening of the first placement groove is in communication with the upward opening of the second placement groove, a first extrusion block is arranged in the first placement groove, and the first placement groove at one side of the first extrusion block is configured for placing an upper rock mass sample, a second extrusion block is arranged in the second placement groove, and the second placement groove at one side of the second extrusion block is configured for placing a lower rock mass sample corresponding in position to the upper rock mass sample;

the first extrusion block comprises a first small wedge having a first adjusting internal thread hole formed in a side wall thereof, a first big wedge, the first small wedge is located on one side of the first big wedge away from the upper rock mass sample, and a surface joint of the first small wedge and the first big wedge is a first inclined plane, and a first adjusting bolt arranged in sequence in the first direction;

wherein a first through hole communicated with the first placement groove is formed in a side wall of the upper fixed shear box, and a threaded end of the first adjusting bolt passes through the first through hole and is threaded to the first adjusting internal thread hole:

the second extrusion block comprises a second small wedge having a second adjusting internal thread hole is formed in a side wall thereof, a second big wedge, the second small wedge is located on one side of the second big wedge away from the lower rock mass sample, and a surface joint of the second small wedge and the second big wedge is a second inclined plane, and a second adjusting bolt;

wherein a second through hole communicated with the second placement groove is formed in a side wall of the lower movable shear box, and a threaded end of the second adjusting bolt passes through the second through hole and is threaded to the second adjusting internal thread hole;

a first elastic sealing element is arranged on each of one side of the first big wedge close to the upper rock mass sample, one side of the first big wedge being close to the lower movable shear box, one side of the second big wedge being close to the lower rock mass sample, and one side of the second big wedge being close to the upper fixed shear box;

after rotation of the first adjusting bolt, the first adjusting bolt is capable of pulling the first small wedge to move towards a direction close to the first adjusting bolt in the second direction, and through the first inclined plane, the movement of the first small wedge is capable of pushing the first big wedge to move towards one side close to the upper rock mass sample in the first direction and to move towards one side close to the lower movable shear box in the third direction;

after rotation of the second adjusting bolt, the second adjusting bolt is capable of pulling the second small wedge to move towards a direction close to the second adjusting bolt in the second direction, and through the second inclined plane, the movement of the second small wedge is capable of pushing the second big wedge to move towards one side close to the lower rock mass sample in the first direction and to move towards one side close to the upper fixed shear box in the third direction;

an elastic capsule made of a corrosion-resistant material is arranged at each of inner walls of both sides of the first placement groove and the second placement groove in the second direction, and a length of the elastic capsule in the first direction is greater than a length of a corresponding upper rock mass sample or lower rock mass sample, and a fluid is able to be injected into the elastic capsule and make the elastic capsule deform elastically with the injection of the fluid;

an upper pressure head device is arranged on the upper fixed box shear and is capable of applying a force in the third direction to the upper rock mass sample in the first placement groove;

a first communicating channel is arranged in the upper fixed shear box, a second communicating channel is arranged in the lower movable shear box, the first communicating channel and the second communicating channel are located on both sides of an entire of the upper rock mass sample and the lower rock mass sample in the first direction, respectively, and both the first communicating channel and the second communicating channel are in communication with a contact gap between the upper rock mass sample and the lower rock mass sample.

2. The shear box for testing shear-seepage coupling characteristics of rock mass according to claim 1, wherein the upper fixed shear box comprises:

a fixed shear slider having a first U-shaped groove penetrating through the second direction formed therein;

a first front side plate, and a first rear side plate are respectively located on both sides of the first U-shaped groove that the first U-shaped groove penetrates through, a first limiting groove is arranged at each of inner sides of both sides of the first U-shaped groove that the first U-shaped groove penetrates through;

a first rear side plate, the first front side plate and the first rear side plate being arranged in parallel in the second direction, and;

wherein first limiting inner protrusions are arranged at one end of each of the first front side plate and the first rear side plate, each of the first limiting inner protrusions are respectively clamped into a corresponding first limiting groove, the first limiting groove corresponding to the first front side plate is capable of limiting a movement of the first front side plate away from the first rear side plate in the second direction, and the first limiting groove corresponding to the first rear side plate is capable of limiting a movement of the first rear side plate away from the first front side plate in the second direction, the first placement groove being formed jointly by the first front side plate, the first rear side plate and the first U-shaped groove;

the lower movable shear box comprises a movable shear slider, a second U-shaped groove penetrating through the second direction is arranged at the movable shear slider, a second limiting groove is arranged at each of inner sides of both sides of the second U-shaped groove that the second U-shaped groove penetrates through;

a second front side plate, and a second rear side plate, the second front side plate and the second rear side are arranged in parallel in the second direction, the second front side plate and the second rear side plate are located on both sides of the second U-shaped groove that the second U-shaped groove penetrates through wherein second limiting inner protrusions are arranged at one end of each of the second front side plate and the second rear side plate, each of the second limiting inner protrusions is respectively clamped into a corresponding second limiting groove, the second limiting groove corresponding to the second front side plate is capable of limiting a movement of the second front side plate away from the second rear side plate in the second direction, and the second limiting groove corresponding to the second rear side plate is capable of limiting a movement of the second rear side plate away from the second front side plate in the second direction, the second placement groove being formed jointly by the second front side plate, the second rear side plate and the second U-shaped groove.

3. The shear box for testing shear-seepage coupling characteristics of rock mass according to claim 1, further comprising a second elastic sealing element arranged on each of an inner wall of one side, opposite to the first big wedge, in the first placement groove, and an inner wall of one side, opposite to the second big wedge, in the second placement groove.

4. The shear box for testing shear-seepage coupling characteristics of rock mass according to claim 1, further comprising:

an accommodating groove arranged on each of inner walls of both sides of the first placement groove and the second placement groove in the second direction, a lower end of the accommodating groove of the first placement groove on one side is in communication with an upper end of the accommodating groove of the second placement groove on a same side, and an elastic capsule is placed in each accommodating groove; and liquid injection ports in communication with the corresponding elastic capsule are formed in outer walls of both sides of the upper fixed shear box and the lower movable shear box in the second direction, respectively.

5. The shear box for testing shear-seepage coupling characteristics of rock mass according to claim 1, wherein the inverted U-shaped frame comprises two connecting posts having lower ends respectively located on two outer side walls of the lower movable shear box in the second direction and are arranged opposite to each other, and a wheel shaft, where upper ends of the two connecting posts are connected by the wheel shaft;

a plurality of bearings are rotatably arranged on the wheel shaft, and a space jointly formed by lower surfaces of each of the bearings, inner sides of the two connecting posts and an upper end surface of the lower movable shear box is configured for the upper fixed shear box to slide in along the first direction.

6. The shear box for testing shear-seepage coupling characteristics of rock mass according to claim 5, further comprising an adjusting mechanism capable of adjusting a position of the wheel shaft in the third direction is arranged on each connecting post.

7. The shear box for testing shear-seepage coupling characteristics of rock mass according to claim 6, wherein the adjusting mechanism comprises a pressure roller block, and a third adjusting bolt;

a U-shaped mounting groove with an upward opening is formed in the upper end of each connecting post, and an end portion of the wheel shaft is placed in each U-shaped mounting groove:

the pressure roller block is fixedly arranged at the opening of each the U-shaped mounting groove;

a threaded hole in threaded connection with the third adjusting bolt is formed in the pressure roller block, and a threaded end of the third adjusting bolt is able to pass through the threaded hole and be abutted against the end portion of the wheel shaft in the U-shaped mounting groove.

8. The shear box for testing shear-seepage coupling characteristics of rock mass according to claim 1, wherein the elastic capsule is made of polytetrafluoroethylene.

9. A method of using the shear box for testing shear-seepage coupling characteristics of rock mass according to claim 1, comprising the following steps of:

(A) preparing an upper rock mass sample and a lower rock mass sample, treating a size of each of the upper rock mass sample and the lower rock mass sample as required, and ensuring that surfaces of the upper rock mass sample and the lower rock mass sample are clean;

(B) placing the upper rock mass sample in a first placement groove of an upper fixed shear box, mounting a first extrusion block on one side of the upper rock mass sample to ensure that a position of the upper rock mass sample is stable; similarly, placing the lower rock mass sample in a second placement groove of a lower movable shear box, and mounting a second extrusion block; and mounting a first sealing element and an elastic capsule at corresponding positions;

(C) mounting a connection limiting part on the lower movable shear box, and sliding the upper fixed shear box into each inverted U-shaped frame above the lower movable shear box in a first direction; and (D) placing an entire shear box assembled in step (C) on a test bench, and adjusting a position of the shear box to ensure stability, enabling a first communicating channel and a second communicating channel to communicate with a water pressure system, and applying a required pressure to the upper rock mass sample through an upper pressure head device, thus starting a test.

* * * * *